United States Patent [19]

Nguyen

[11] Patent Number: 4,997,473
[45] Date of Patent: Mar. 5, 1991

[54] CERTAIN 2-(2'-SUBSTITUTED BENZOYL)-4-PROPAROYL-1,3-CYCLOHEXANEDIONE HERBICIDES

[75] Inventor: Nhan H. Nguyen, Hercules, Calif.

[73] Assignee: ICI Americas Inc., Wilmington, Del.

[21] Appl. No.: 398,037

[22] Filed: Aug. 24, 1989

[51] Int. Cl.$^5$ ............................................. A01N 31/00
[52] U.S. Cl. ............................................. 71/98; 71/103; 558/415; 560/12; 560/13; 560/18; 564/85; 564/86; 564/88; 568/30; 568/31; 568/36; 568/37
[58] Field of Search ............ 568/30, 31, 36, 37, 568/27, 28, 42, 43; 558/415; 560/12, 13, 18; 564/87, 86, 85; 71/98, 103

[56] References Cited

U.S. PATENT DOCUMENTS

| 4,762,551 | 8/1988 | Knudsen | 71/103 |
| 4,783,213 | 11/1988 | Lee | 71/98 |
| 4,853,028 | 8/1989 | Carter et al. | 71/103 |

FOREIGN PATENT DOCUMENTS

| 0135191 | 3/1985 | European Pat. Off. | 568/31 |
| 0264859 | 4/1988 | European Pat. Off. | 568/31 |
| 0268795 | 6/1988 | European Pat. Off. | 568/37 |

Primary Examiner—Werren B. Lone
Attorney, Agent, or Firm—Edwin H. Baker

[57] ABSTRACT

Compunds of the formula

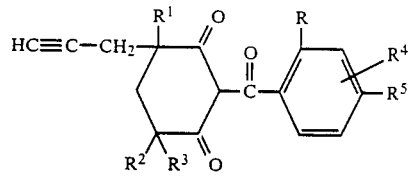

wherein R is halogen, $C_1$-$C_2$ alkyl, nitro, $C_1C_2$ haloalkyl, $C_1$-$C_2$ alkoxy, $C_1$-$C_2$ alkylthio or $C_1C_2$ alkylsulfonyl: $R^1$ is hydrogen or $C_1$-$C_2$ alkyl; $R^2$ is hydrogen or $C_1$-$C_2$ alkyl; $R^3$ is hydrogen or $C_1$-$C_2$ alkyl; and $R^4$ and $R^5$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$- wherein n is the integer 0, 1 or 2; and $R^b$ is (a) $C_1$-$C_4$ alkyl, (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^3C(O)$- wherein $R^3$ is $C_1$-$C_4$ alkyl or $C_1$-$C_4$ alkoxy; or (12) —$SO_2NR^cR^d$ wherein $R^c$ and $R^d$ are as defined; and (13) —$N(R^c)C(O)R^d$ wherein $R^c$ and $R^d$ are as defined.

21 Claims, No Drawings

CERTAIN 2-(2'-SUBSTITUTED BENZOYL)-4-PROPAROYL-1,3-CYCLOHEXANEDIONE HERBICIDES

BACKGROUND OF THE INVENTION

European Patent Publication Nos. 0 135 191, 0 186 117, 0 186 118, 0 186 119 and 0 186 120 relate to certain herbicidal compounds that have the structural formula

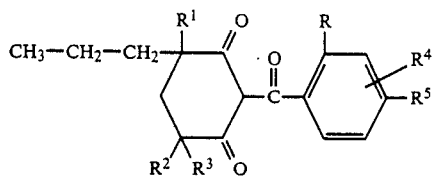

wherein R through $R^5$ are substantially as defined below.

DESCRIPTION OF THE INVENTION

This invention relates to 2-(2'-substituted benzoyl)-4-propargyl-1,3-cyclohexandediones and their use as herbicides.

One embodiment of this invention is an herbicidal composition comprising an herbicidally active 2-(2'-substituted benzoyl)-4-propargyl-1,3-cyclohexanedione and an inert carrier therefor. The 4-and 6-positions of the 4-propargyl-1,3-cyclohexanedione moiety are preferably substituted with groups hereinafter defined, most preferably with hydrogen or methyl groups. The substituted benzoyl moiety can be further substituted, preferably with the groups hereinafter recited.

Also embodied within the scope of this invention are novel compounds having the following structural formula

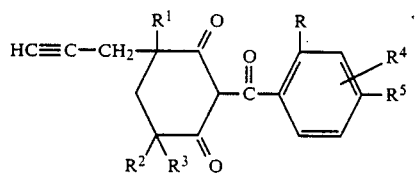

wherein

R is halogen, preferably chlorine or bromine; $C_1$-$C_2$ alkyl, preferably methyl; nitro; $C_1$-$C_2$ haloalkyl, preferably trifluoromethyl; $C_1$-$C_2$ alkoxy, preferably methoxy; $C_1$-$C_2$ alkylthio, preferably methylthio; and $C_1$-$C_2$ alkylsulfonyl, preferably methylsulfonyl. Preferably R is chlorine, bromine, or nitro;

$R^1$ is hydrogen or $C_1$-$C_2$ alkyl, preferably methyl;
$R^2$ is hydrogen or $C_1$-$C_2$ alkyl, preferably methyl;
$R^3$ is hydrogen or $C_1$-$C_2$ alkyl, preferably methyl; and $R^4$ and $R^5$ independently are (1) hydrogen; (2) halogen, preferably chlorine, fluorine, or bromine; (3) $C_1$-$C_4$ alkyl, preferably methyl; (4) $C_1$-$C_4$ alkoxy, preferably methoxy; (5) trifluoromethoxy; (6) cyano; (7) nitro; (8) $C_1$-$C_4$ haloalkyl, more preferably trifluoromethyl; (9) $R^bSO_n$— wherein n is the integer 0, 1, or 2, preferably 2; and $R^b$ is
 (a) $C_1$-$C_4$ alkyl, preferably methyl;
 (b) $C_1$-$C_4$ alkyl substituted with halogen or cyano, preferably chloromethyl, trifluoromethyl or cyanomethyl;
 (c) phenyl; or
 (d) benzyl;
(10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) —$SO_2NR^cR^d$ wherein $R^c$ and $R^d$ are as defined; or (13) —$N(R^c)$-$C(O)R^d$ wherein $R^c$ and $R^d$ are as defined.

Preferably $R^4$ is in the 3-position. More preferably $R^4$ is hydrogen, chlorine, fluorine, trifluoromethyl, cyano, $C_1$-$C_4$ alkoxy or $C_1$-$C_4$ thioalkyl. Most preferably, $R^4$ is hydrogen. Preferably $R^5$ is hydrogen, halogen, cyano, trifluoromethyl or $R^bSO_2$ wherein $R^b$ is $C_1$-$C_4$ preferably methyl or $C_1$-$C_4$ haloalkyl, preferably chloromethyl, difluoromethyl, or trifluoromethyl.

The term "$C_1$-$C_4$ alkyl" includes methyl, ethyl, n-propyl, isopropyl, n-butyl, sec-butyl, isobutyl, and t-butyl. The term "halogen" includes chlorine, bromine, iodine, and fluorine. The term "$C_1$-$C_4$ alkoxy" includes methoxy, ethoxy, n-propoxy, isopropoxy, n-butoxy, sec-butoxy, isobutoxy, and t-butoxy. The term "$C_1$-$C_4$ haloalkyl" includes the alkyl groups defined above under $C_1$-$C_4$ alkyl in which one or more hydrogens is replaced by chlorine, bromine, iodine, or fluorine.

Salts of the above-described compounds (as defined hereinafter) are included within the scope of this invention.

The compounds of this invention can have the following four structural formulae because of tautomerism:

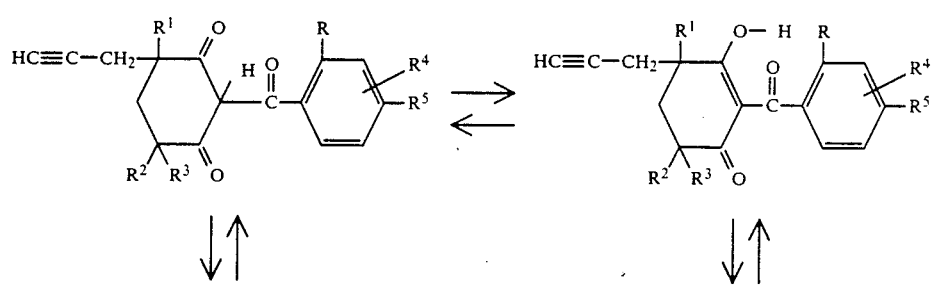

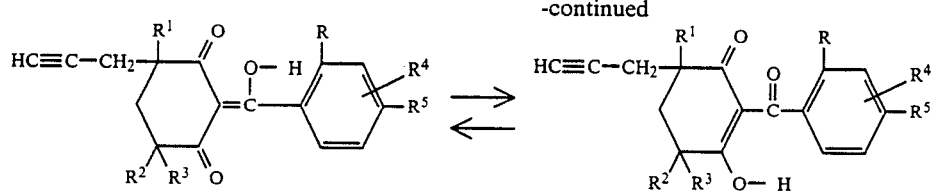

wherein R, $R^1$, $R^2$, $R^3$, $R^4$, and $R^5$ are as defined above.

The circled proton on each of the four tautomers is reasonably labile. These protons are acidic and can be removed by reaction with a base to form a salt having an anion of the following four resonance forms:

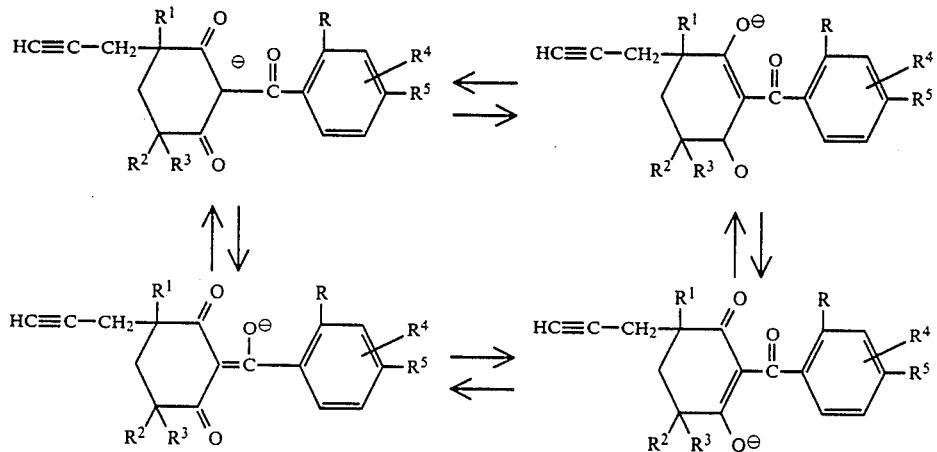

wherein R, $R^1$, $R^2$, $R^3$, $R^4$, and $R^5$ are as defined above.

Examples of cations of these bases are inorganic cations such as alkali metals, e.g., lithium, sodium and potassium; the alkaline earth metals, e.g. calcium and magnesium or ammonium or organic cations such as substituted ammonium, sulfonium, sulfoxonium or phosphonium wherein the substituents are aliphatic or aromatic groups.

Those skilled in the art will recognize in considering the salts of this invention that varying degrees of association between the anion and cation will exist depending upon the nature of the cation. In some instances with a suitable cation, such as copper, the salt can exist in a chelated form.

The compounds of this invention and their salts are active herbicides of a general type. That is, they are herbicidally effective against a wide range of plant species. The method of controlling undesirable vegetation of the present invention comprises applying an herbicidally effective amount of the above-described compounds or their salts to the area where control is desired.

The compounds of the present invention can be prepared by the following two-step general method.

The process proceeds via the production of an enol ester intermediate as shown in reaction (1). The final product is obtained by rearrangement of the enol ester as shown in reaction (2).

The process is conducted in the presence of a catalytic amount of a source of cyanide anion and/or hydrogen cyanide, together with a molar excess, with respect to the enol ester, of a moderate base.

The two reactions may be conducted as separate steps by isolation and recovery of enol ester using conventional techniques prior to conducting step (2), or by addition of a cyanide source to the reaction medium after the formation of the enol ester, or in one step by inclusion of the cyanide source at the start of reaction (1).

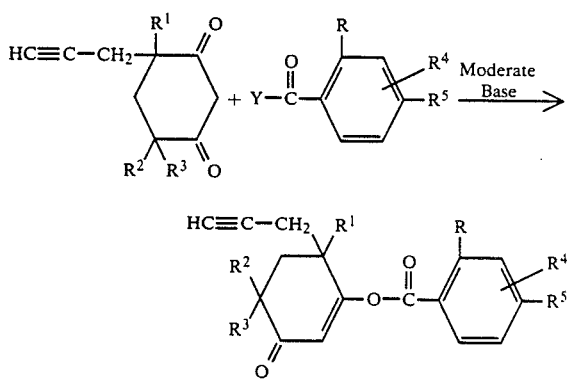

wherein R through $R^5$ and moderate base are as defined and Y is halogen, preferably chlorine, $C_1$-$C_4$ alkyl—C(O)—O—, $C_1$-$C_4$ alkoxyC(O)—O— or

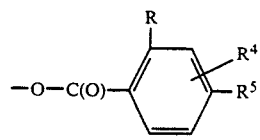

R, $R^4$, and $R^5$ in this portion of the molecule are identical with those in the reactant shown above and the moderate base is as defined, preferably tri-$C_1$-$C_6$ alkylamine, alkali metal carbonate, or alkali metal phosphate.

Generally, in step (1) mole amounts of the dione and substituted benzoyl reactant are used, along with a mole amount or excess of the moderate base. The two reactants are combined in an organic solvent such as methylene chloride, toluene, ethyl acetate or dimethylformamide. The base or benzoyl reactant preferably is added to the reaction mixture with cooling. The mixture is stirred at 0–50° C. until the reaction is substantially completed.

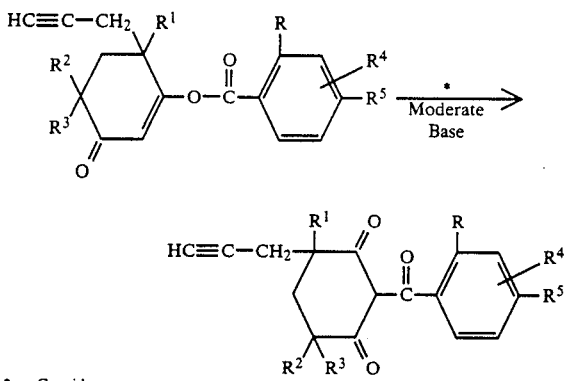

* = Cyanide source.

wherein the moderate base and R through $R^5$ are as defined above.

Generally, in step (2) a mole of the enol ester intermediate is reacted with 1 to 4 moles of the moderate base, preferably about 2 moles of moderate base and from 0.01 mole to about 0.5 mole or higher, preferably about 0.01–0.1 mole of the cyanide source. The mixture is stirred in a reaction pot until the rearrangement is substantially completed at a temperature below 50° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; benzaldehyde cyanohydrin; cyanohydrins of $C_2$–$C_5$ aliphatic aldehydes such as acetaldehyde cyanohydrin, propionaldehyde cyanohydrin, etc.; cyclohexanone cyanohydrin; lactonitrile; zinc cyanide; di- and tri-(lower alkyl) silyl cyanides, notably dimethyl- and trimethylsilyl cyanide; potassium ferric cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher levels of about 2 mole percent. Generally about 1–10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as N,N-dimethylaniline (which would not function effectively). Moderate bases suitable for use in this embodiment include both organic bases, e.g., trialkylamines such as triethylamine and inorganic bases such as alkali metal carbonates and phosphates. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the crown ethers.

A number of different solvents are useful in this process, depending on the nature of the acid halide or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can prepared from the corresponding substituted benzoic acids according to the teaching of *Reagents for Organic Synthesis*, Vol. I. L. F. Fieser and M. Fieser, pp. 767–769 (1967).

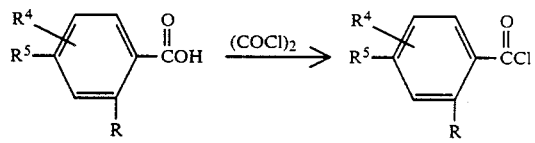

wherein R, $R^4$ and $R^5$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are three representative examples of the methods described therein.

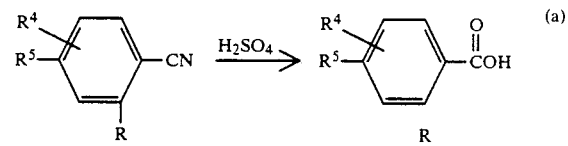

wherein R, $R^4$ and $R^5$ are as previously defined. In reaction (a) the substituted benzonitrile is heated to reflux in aqueous sulfuric acid for several hours. The mixture is cooled and the reaction product is isolated by conventional techniques.

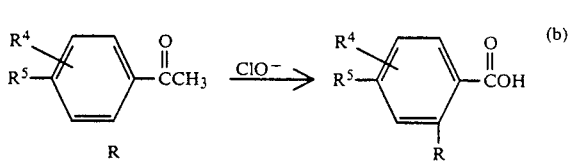

wherein R, $R^4$ and $R^5$ are as previously defined. In reaction (b) the substituted acetophenone is heated to reflux for several hours in an aqueous hypochlorite solution. The mixture is cooled and the reaction product is isolated by conventional techniques.

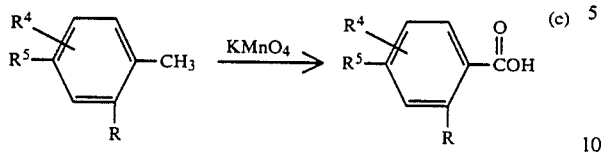
(c)

wherein R, R[4] and R[5] are as previously defined. In reaction (c) the substituted toluene is heated to reflux in an aqueous solution of potassium permanganate for several hours. The solution is then filtered and the reaction product is isolated by conventional techniques.

The 4-propargyl-1,3-cyclohexanediones can prepared via reaction of a 4- and/or 6- substituted or unsubstituted 1,3-cyclohexanedione with n-butyllithium in a solvent such as tetrahydrofuran to deprotonate the 2- and 4-carbon atoms of the 1,3-cyclohexanedione compound. Thereafter the deprotonated dione is reacted with propargyl bromide in a solvent such as toluene.

EXAMPLE 1

4-Propargyl-1,3-cyclohexanedione

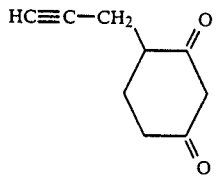

n-Butyllithium [2.54 molar (M), 35.6 milliters (mL), 89.0 mmol]) was added dropwise to a solution of 1,3-cyclohexanedione [5.0 grams (g), 44.6 mmol] in tetrahydrofuran (100 mL) at −78° C. The reaction mixture was warmed to 0° C. and maintained at that temperature for 1.5 hours. The mixture was cooled to −78° C. and propargyl bromide (80% toluene solution, 5 mL, 45.0 mmol) was added. The mixture was warmed slowly to room temperature and stirred overnight. Thin layer chromatography analysis (silica:1:1 ethyl acetate:hexanes-1% acetic acid) indicated the synthesis of a new product along with the cyclohexanedione. The mixture was cooled to 0° C. and aqueous 5% potassium carbonate (K$_2$CO$_3$) was added. All acidic materials were extracted into the basic layer. The latter was then back-extracted with diethyl ether. The basic layer was acidified at 0° C. with concentrated hydrochloric acid (HCl) and the organic materials were extracted into methylene chloride. The organic layer was dried over magnesium sulfate (MgSO$_4$), filtered and concentrated to an oil. Flash column chromatograph purification yielded the desired product (2.3 g, white solid) whose structure was confirmed by nuclear magnetic resonance, infrared spectroscopy, and mass spectroscopy analyses.

EXAMPLE 2

2-(2'-Nitro-4'-methylsulfonylbenzoyl)-4-propargyl-1,3-cyclohexanedione

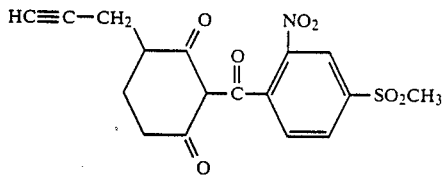

4Propargyl-1,3-cyclohexanedione (3.75 g, 25 mmol) and 4-methanesulfonyl-2-nitrobenzoyl chloride (6.06 g, 23 mmol) were dissolved in acetonitrile (100 mL) at 0° C. Triethylamine (9.6 mL, 69 mmol) was added. The mixture was then stirred for 3 hours. To the mixture was then added potassium cyanide (5.0 g) and 18-crown-6 ether (0.5 g) in one portion. The mixture was stirred for 3 days. After dilution with ether, the solution was washed with 1N HCl and extracted with 5% K$_2$CO$_3$. The basic extract was acidified with concentrated HCl and extracted with diethyl ether. The ether extract was washed with brine, dried over MgSO$_4$, and concentrated under vacuum, yielding 3.9 g of the desired product, an orange solid, m.p. 65-70° C. The structure was confirmed by nuclear magnetic spectroscopy, infrared spectroscopy, and mass spectroscopy.

The following is a table of certain selected compounds that are prepared according to the procedures described herein. Compound numbers are assigned to each compound and are used throughout the remainder of the application.

TABLE I

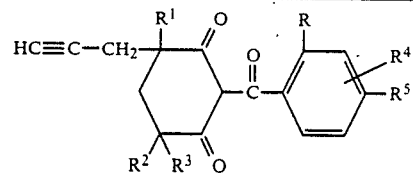

| Cmpd. No. | R | R[1] | R[2] | R[3] | R[4] | R[5] | melting point |
|---|---|---|---|---|---|---|---|
| 1 | NO$_2$ | H | H | H | H | 4-CF$_3$ | oil |
| 2 | Cl | H | H | H | H | 4-SO$_2$CH$_3$ | 57-61° C. |
| 3[a] | NO$_2$ | H | H | H | H | 4-SO$_2$CH$_3$ | 65-70° C. |
| 4 | NO$_2$ | H | H | H | H | H | oil |
| 5 | NO$_2$ | H | CH$_3$ | CH$_3$ | H | 4-CF$_3$ | 80-83° C. |
| 6 | NO$_2$ | H | CH$_3$ | CH$_3$ | H | 4-Cl | oil |
| 7 | NO$_2$ | H | CH$_3$ | CH$_3$ | H | 4-SO$_2$CH$_3$ | 70-75° C. |

[a]Prepared in Example 2.

The following Table shows the instrumental analysis spectral data for the compounds of Table I.

TABLE I-A

| Compound Number | Spectral Data |
|---|---|
| 1 | H-NMR, (CDCl$_3$): δ 1.8-3.1 (m, 8H), 7.23 (d, 1H), 7.60 (m, 1H), 7.72 (m, 1H), 8.22 (d, 1H), 16.6 (s, 1H)<br>IR (film): ν (cm$^{-1}$) 3300, 2960, 2940, 2120, 1680, 1570, 1540, 1415, 1350, 860, 820, 790, 760, 710<br>MS (m/z): 51 (100), 55 (53), 65 (55), 79 (65), 103 (53), 150 (62), 253 (37, M$^+$-NO$_2$), 271 (12, M$^+$-CO) |
| 2 | H-NMR (CDCl$_3$): δ 1.9-3.1 (m, 5H), 1.92 (t, 1H), 2.98 (dd, 2H), 7.38 (d, 1H), 7.97 (dd, 1H), 8.49 (d, 1H), 16.23 (s, 1H), 16.83 (s, 1H) |

TABLE I-A-continued

| Compound Number | Spectral Data |
|---|---|
| | IR (film): $\nu$ (cm$^{-1}$) 3310, 3120, 2970, 2900, 2135, 1685, 1610, 1570, 1540, 1510, 1420, 1365, 1335, 1260, 1190, 1170, 1145, 1095, 950, 920, 855, 825, 800, 775, 715<br>MS (m/z): 55 (90), 65 (64), 79 (100), 218 (34), 253 (12), 281 (28), 321 (70, M$^+$-NO$_2$) |
| 3 | H-NMR (CDCl$_3$): $\delta$ 1.9-3.0 (m, 5H), 1.99 (t, 1H), 2.91 (m, 2H), 3.10 (s, 3H), 7.38 (d, 1H), 7.89 (dd, 1H), 7.96 (d, 1H), 16.67, 17.26 (2s, 1H)<br>IR (KBr Pellet): $\nu$ (cm$^{-1}$) 3300, 3090, 3010, 2960, 2940, 2860, 1680, 1600, 1565, 1430, 1320, 1160, 960, 840, 790, 750<br>MS (m/z): 55 (47), 69 (64), 155 (64), 217 (30), 219 (12), 291 (25), 331 (100, M$^+$-Cl) |
| 4 | H-NMR (CDCl$_3$): $\delta$ 1.9-3.0 (m, 5H), 1.96 (t, 1H), 2.91 (m, 2H), 3.17 (s, 3H), 7.45 (d, 1H), 8.26 (dd, 1H), 8.75 (d, 1H), 16.10, 16.72 (2s, 1H)<br>IR (KBR Pellet): $\nu$ (cm$^{-1}$) 3300, 3080, 3020, 2940, 2860, 1680, 1600, 1570, 1540, 1420, 1360, 1320, 1170, 1150, 970, 780, 765, 730<br>MS (m/z): 55 (87), 63 (74), 69 (49), 79 (100), 103 (38), 228 (14), 264 (13), 291 (14), 331 (42, M$^+$-NO$_2$) |
| 5 | H-NMR (CDCl$_3$): $\delta$ 1.05, 1.13, 1.43, 1.48 (4s, 6H), 1.83-3.15 (m, 6H), 7.40 (d, 1H), 7.95 (dd, 1H), 8.48 (d, 1H), 16.79, 16.81 (2s, 1H)<br>IR (KBr DRIFT): $\nu$ (cm$^{-1}$) 3320, 3080, 3030, 2980, 2110, 1672, 1566, 1537, 1406, 1381, 1356, 1327, 1141, 642, 624<br>MS (m/z): 55 (36), 65 (34), 70 (67), 79 (100), 91 (52), 218 (22), 349 (78, M$^+$-NO$_2$), 366 (3, M$^+$-Et), 376 (3, M$^+$-F) |
| 6 | H-NMR (CDCl$_3$): $\delta$ 1.04, 1.11, 1.41. 1.47 (4s, 6H), 1.80-3.12 (m, 6H), 7.19 (d, 1H), 7.66 (dd, 1H), 8.18 (d, 1H), 16.96, 16.99 (2s, 1H)<br>IR (film): $\nu$ (cm$^{-1}$) 3297, 3090, 2970, 2931, 2140, 1671, 1559, 1531, 1406, 1383, 1350, 987, 965, 888, 837, 662<br>MS (m/z): 53 (50), 65 (46), 69 (71), 79 (100), 91 (54), 110 (37), 138 (39), 184 (29), 315 (16 M$^+$-NO$_2$), 317 (6) |
| 7 | H-NMR (CDCl$_3$): $\delta$ 1.04, 1.13, 1.43, 1.49 (4s, 6H), 1.8-2.31 (m, 4H), 2.52-2.81 (m, 2H), 3.17 (s, 3H), 7.46 (d, 1H), 8.26 (dd, 1H), 8.75 (d, 1H), 16.61, 16.63 (2s, 1H)<br>IR (KBr DRIFT:): $\nu$ (cm$^{-1}$) 3288, 3080, 2970, 2927, 2130, 1666, 1561, 1555, 1532, 1352, 1317, 1162, 1146, 961, 760, 664, 531<br>MS (m/z): 55 (32), 65 (33), 69 (53), 79 (100), 91 (51), 103 (25), 228 (13), 359 (90, M$^+$-NO$_2$) |

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence Herbicide Test. On the day preceding treatment, seeds of ten different weed species were planted in loamy sand soil in individual rows using one species per row across the width of a flat. The seeds used were giant foxtail (FT) (*Setaria faberi*), annual ryegrass (ARG) (*Lolium multiflorum*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), yellow nutsedge (YNS) (*Cyperus esculentus*), broadleaf signalgrass (BSG) (*Brachiaria platyphylla*), cocklebur (CB) (*Xanthium pensylvanicum*) and sicklepod (SP) (*Cassia obtusifolia*). Ample seeds were planted to give about 5 to 30 seedlings per row, after emergence, depending upon the size of the plants.

Using a top-loader, 25 milligrams (mg) of the compound to be tested were weighed out into a 70 mL wide-mouth clear bottle and dissolved in 20 mL of acetone plus 20 mL water containing enough polyoxyethylene sorbitan monolaurate emulsifier to give a final solution of 0.5% (v/v). The solution was then sprayed onto a seeded flat on a linear spray table calibrated to deliver 400 liters per hectare (L/ha). The application rate was 0.28 kg/ha.

After treatment, the flats were placed in a greenhouse at a temperature of 70 to 80° F. and watered by sprinkling. Sixteen to twenty-one days after treatment, the degree of injury or control was determined by comparison with untreated check plants of the same age. The injury rating from 0 to 100% was recorded for each species as percent control with 0% representing no injury and 100% representing complete control.

The results of these tests are shown in the following Table II.

TABLE II

Pre-Emergence Multi-Weed Herbicide Test
Application Rate - 0.28 kg/ha

| Cmpd. No. | FT | ARG | WG | WO | BSG | AMG | VL | SP | YNS | CB |
|---|---|---|---|---|---|---|---|---|---|---|
| 1 | 90 | 75 | 100 | 50 | 100 | 90 | 100 | 60 | 85 | 50 |

TABLE II-continued

Pre-Emergence Multi-Weed Herbicide Test
Application Rate - 0.28 kg/ha

| Cmpd. No. | FT | ARG | WG | WO | BSG | AMG | VL | SP | YNS | CB |
|---|---|---|---|---|---|---|---|---|---|---|
| 1 | 0 | 0 | 0 | 0 | 50 | 30 | 100 | 40 | 30 | 20 |
| 3 | 100 | 35 | 100 | 40 | 100 | 100 | 100 | 60 | 95 | 50 |
| 4 | 0 | 5 | 60 | 20 | N | 25 | 70 | 0 | 0 | 0 |
| 5 | 95 | 70 | 100 | 40 | 95 | 85 | 100 | 40 | 90 | 95 |
| 6 | 100 | 60 | 100 | 25 | 100 | 65 | 100 | 10 | 85 | 85 |
| 7 | 100 | 90 | 100 | 85 | 100 | 100 | 100 | 80 | 90 | 100 |

N = Not Rated.

Post-Emergence Herbicide Test: This test was conducted in an identical manner to the testing procedure for the pre-emergence herbicide test, except the seeds of the nine different weed species were planted 10–12 days before treatment. Also, watering of the treated flats was confined to the soil surface and not to the foliage of the sprouted plants.

The results of the post-emergence herbicide test are reported in Table III.

TABLE III

Post-Emergence Multi-Weed Herbicide Test
Application Rate - 0.28 kg/ha

| Cmpd. No. | FT | ARG | WG | WO | BSG | AMG | VL | SP | YNS | CB |
|---|---|---|---|---|---|---|---|---|---|---|
| 1 | 70 | 70 | 100 | 80 | 85 | 100 | 100 | 85 | 85 | 95 |
| 2 | 50 | 50 | 95 | 50 | 50 | 100 | 100 | 80 | 85 | 60 |
| 3 | 80 | 80 | 100 | 70 | 95 | 100 | 100 | 90 | 90 | 100 |
| 4 | 20 | 50 | 40 | 15 | 50 | 80 | 90 | 5 | 30 | 40 |
| 5 | 80 | 50 | 85 | 75 | 95 | 90 | 100 | 50 | 60 | 95 |
| 6 | 40 | 30 | 90 | 30 | 95 | 40 | 100 | 20 | 60 | 80 |
| 7 | 100 | 85 | 90 | 100 | 100 | 90 | 100 | 40 | 80 | 85 |

(—) = No Test Results.

The compounds of the present invention and their salts are useful as herbicides and can be applied in a variety of ways at various concentrations. In practice, the compounds or salts are formulated into herbicidal compositions, by admixture, in herbicidally effective amounts, with the adjuvants and carriers norm ally employed for facilitating the dispersion of active ingredients for agricultural applications, recognizing the fact that the formulation and mode of application of a toxicant may affect the activity of the materials in a given application. Thus, these active herbicida compounds or salts can be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient. A herbicidally effective amount depends upon the nature of the seeds or plants to be controlled and the rate of application varies from about 0.01 to approximately 10 pounds per acre, preferably from about 0.02 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wettable organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound or salt with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which may be coated with the toxicant. Granular formulations normally are prepared to contain from about 1% to about 25% of active ingredients which may include surface-active agents such as heavy aromatic naphtha, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their salts; polyhydric alcohols; polyethoxylated alcohols; esters and fatty amines; and other types of surface-active agents, many of which are available in commerce. The surface-active agent, when used, normally comprises from 0.1% to 15% by weight of the herbicidal composition.

Dusts, which are free-flowing admixtures of the active ingredients with finely divided solids such as talc, clays, flours and other organic and inorganic solids which act as dispersants and carriers for the toxicant, are useful formulations for soilincorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging, or mixing operations. In the following examples the herbicidal compound can be substituted with the herbicidal salt of the compound.

| General Formula with Ranges | | Specific Formula | |
|---|---|---|---|
| EMULSIFIABLE CONCENTRATE FORMULATIONS | | | |
| herbicidal compound | 5–55 | herbicidal compound | 24 |
| surfactant(s) | 5–25 | proprietary blend of oil-soluble sulfonates and polyoxyethylene ethers | 10 |
| solvent(s) | 20–90 | | |
| | 100% | polar solvent | 27 |
| | | petroleum hydrocarbon | 39 |
| | | | 100% |
| WETTABLE POWDER FORMULATIONS | | | |
| herbicidal compound | 3–90 | herbicidal compound | 80 |
| wetting agent | 0.5–2 | sodium dialkyl naphthalene sulfonate | 0.5 |
| dispersing agent | 1–8 | | |
| diluent(s) | 8.5–87 | sodium lignosulfonate | 7 |
| | 100% | attapulgite clay | 12.5 |
| | | | 100% |
| EXTRUDED GRANULAR FORMULATIONS | | | |
| herbicidal compound | 1–20 | herbicidal compound | 10 |
| binding agent | 0–10 | lignin sulfonate | 5 |
| diluent(s) | 70–99 | calcium carbonate | 85 |
| | 100% | | 100% |
| FLOWABLE FORMULATIONS | | | |
| herbicidal compound | 20–70 | herbicidal compound | 45 |
| surfactant(s) | 1–10 | polyoxyethylene ether | 5 |
| suspending agent(s) | 0.05–1 | attagel | 0.05 |
| antifreeze agent | 1–10 | propylene glycol | 10 |
| antimicrobial agent | 1–10 | 1,2-benzisothiazoline-3-one | 0.03 |
| antifoam agent | 0.1–1 | | |
| solvent | 7.95–77.85 | silicone defoamer | 0.02 |
| | 100% | water | 39.9 |
| | | | 100% |

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used The phytotoxic compositions of this invention can be applied to the plants in any conventional manner. Thus, the dust and liquid compositions can be applied to the plant by the use of power dusters, boom and hand sprayers and spray dusters. The compositions can also be applied from airplanes as a dust or a spray or by rope wick applications because they are effective in very low dosages. In order to modify or control growth of germinating seeds or emerging seedlings, as a typical example, the dust and liquid compositions can be applied to the soil according to conventional methods and can be distributed in the soil to a depth of at least ½ inch below the soil surface. It is not necessary that the phytotoxic compositions be mechanically admixed with the soil particles since these compositions can also be applied merely by spraying or sprinkling the surface of the soil. The phytotoxic compositions of this invention can also When salts are used as the active ingredient in the herbicidal compositions of this invention it is recommended to use salts that are agriculturally acceptable.

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

The herbicidal compounds of this invention can be used in combination with other herbicidal compounds for broader spectrum control of undesirable vegetation. Examples of other herbicidal compounds are as follows:
1 ANILIDES
1 ANILIDES
Alachlor — 2—chloro—2',6'—diethyl—N—(methoxymethyl)acetanilide
Metolachlor — 2—chloro—N—(2—ethyl—6—methylphenyl)—N—(2—methoxy—1—methy lethyl)acetamide
Propanil — N—(3,4—dichlorophenyl)propionanilide
2. TRIAZINES
Atrazine —2—chloro—4—(ethylamino)—6—isopropylamino)—s—triazine
Cyanazine — 2—chloro—4—(1—cyano—1—methylethylamino)—6—ethylamino—s—triazi ne Metribuzin — 4—amino—6—tert—butyl—3—(methylthio)—1,2,4—triazin—5(4H)—one

3. THIOCARBAMATES

Molinate — S—ethyl hexahydro—1 H—azepine—1—carbothioate

Butylate — S—ethyl diisobutylthiocarbamate

4. UREAS

Monuron — 3—(p—chlorophenyl)—1,1—dimethylurea

Linuron — 3—(3,4—dichlorophenyl)—1—methoxy—1—methylurea

5. TOLUIDINES

Trifluralin — α,α,α—trifluoro—2,6—dinitro—N,N—dipropyl—p—toluidine

Pendimethalin — N—(1—ethylpropyl)—3,4—dimethyl—2,6—dinitrobenzeneamine

6. HORMONES 2,4—D — (2,4—dichlorophnoexy) acetic acid

MCPA — (2—methyl—4—chlorophenoxy) acetic acid

7. DIAZINES

Bentazon — 3—isopropyl—1H —2,3,1—benzothiadiazin—4(3H)—one 2,2—dioxide

Oxadiazon — 2—tert—butyl—4—(2,4—dichloro—5—isopropoxyphenyl)—$\Delta^2$1,3,4'3 oxadiazolin—5—one

8. DIPHENYL ETHERS

Acifluorfen — sodium 5—[2—chloro—4—(trifluoromethyl)phenoxy]—2—nitrobenzoate

Fluazifop—butyl —(±)—butyl 2—[4[(5—(trifluoromethyl)—2—pyridinyl)oxy]phenoxy]propan oate Chlomethoxynil — 2,4—dichlorophenyl 3—methoxy—4—nitrophenyl ether

9. IMIDAZOLINONES

Imazaquin — 2—[4,5—dihydro—4—methyl—4—(-1—methylethyl)—5—oxo—1 H—imidazol—2—yl-]—3—quinolin carboxylic acid

10. SULFONYL UREAS

Bensulfuron methyl — methyl 2—[[[[[(4,6—dimethoxypyrimidin—2—yl)amino]carbonyl]amino]sul fonyl]methyl]benzoate Chlorimuron ethyl — ethyl 2—(((((4—chloro—6—methoxypyrimidin—2—yl)amino)carbonyl)amino)sulf onyl) benzoate

11. MISCELLANEOUS COMPOUNDS

Dimethazone — 2—(2—chlorophenyl)methyl—4,4—dimethyl—3—isoxazolidinone

Norflurazon — 4—chloro—5—(methylamino)—2—α,α,α—trifluoro—m—tolyl)—3—(b 2H)—pyridazinone Dalapon — 2,2—dichloropropionic acid Glyphosate — isopropyl amine salt of N—(phosphonomethyl) glycine Fenoxaprop—ethyl — (+)—ethyl—2,4—((6—chloro—2—benzoxazolyloxy)phenoxy)propanoate

What is claimed is:

1. Compounds of the formula

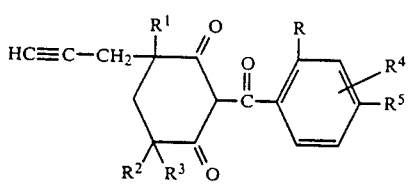

wherein

R is halogen, $C_1$-$C_2$ alkyl, nitro, $C_1$-$C_2$ haloalkyl, $C_1$-$C_2$ alkoxy, $C_1$-$C_2$ alkylthio, or $C_1$-$C_2$ alkylsulfonyl;

$R^1$ is hydrogen or $C_1$-$C_2$ alkyl;

$R^2$ is hydrogen or $C_1$-$C_2$ alkyl;

$R^3$ is hydrogen or $C_1$—$C_2$ alkyl; and $R^4$ and $R^5$ independently are (1) hydrogen; (2) halogen; (3) $C_1$-$C_4$ alkyl; (4) $C_1$-$C_4$ alkoxy; (5) trifluoromethoxy; (6) cyano; (7)nitro; (8) C -$C_{nitro;}$ (8) $C_1$-$C_4$ haloalkyl; (9) $R^bSO_n$- wherein n is the integer 0, 1 or 2; and is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^3C(O)$—wherein $R^3$ is $C_1$-$C_4$ alkyl or $C_1$-$C_4$ alkoxy; or (12) —$SO_2NR^cR^d$ wherein $R^c$ and $R^d$ are as defined; and (13) —$N(R^c)C(O)R^d$ wherein $R^c$ and $R^d$ are as defined.

2. The compounds of claim 1 wherein R is chlorine, bromine, methyl, nitro or trifluoromethyl; $R^1$, $R^2$ and $R^3$ are hydrogen or methyl; and $R^5$ and $R^6$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$wherein $R^e$ is $C_1$-$C_4$ alkyl or $C_1$-$C_4$ alkoxy; or (12) $SO_2NR^cR^d$ wherein $R^c$ and $R^d$ are as defined; or (13) —N—($R^c$)-$C(O)R^d$ wherein $R^c$ and $R^d$ are as defined.

3. The compounds of claim 2 wherein $R^4$ and $R^5$ independently are hydrogen; chlorine; fluorine; bromine; methyl; $C_1$-$C_4$ alkoxy; trifluoromethoxy; cyano; nitro; trifluoromethyl; $R^bSO_n$— wherein n is the integer 0 or 2 and $R^b$ is methyl, ethyl, chloromethyl, trifluoromethyl, ethyl or n—propyl, $R^eC(O)$—wherein $R^e$ is $C_1$-$C_4$ alkyl; or $SO_2CR^cR^d$ wherein $R^c$ and $R^d$ are as defined, and $R^4$ is in the 3-position and $R^5$ is in the 4position.

4. The compounds of claim 2 wherein $R^4$ is hydrogen and $R^5$ is hydrogen, chlorine, bromine, fluorine, cyano, trifluoromethyl or $R^bSO_2$ wherein $R^b$ is $C_1$-$C_4$ alkyl or $C_1$-$C_4$ haloalkyl.

5. The compound of claim 2 wherein R is nitro, $R^1$ is hydrogen; $R^2$ is hydrogen; $R^3$ is hydrogen; $R^4$ is hydrogen; and $R^5$ is trifluoromethyl.

6. The compounds of claim 2 wherein R is nitro; $R^1$ is hydrogen; $R^2$ is hydrogen; $R^3$ is hydrogen; $R^4$ is hydrogen; and $R^5$ is methylsulfonyl.

7. The compound of claim 2 wherein R is nitro; $R^1$ is hydrogen; $R^2$ is methyl; $R^3$ is methyl; $R^4$ is hydrogen; and $R^5$ is methylsulfonyl.

8. The method of controlling undesirable vegetation comprising applying to the area where control is desired, an herbicidally effective amount of a compound having the formula

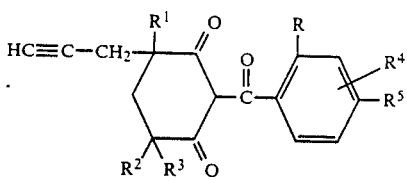

wherein

R is halogen, $C_1$–$C_2$ alkyl, nitro, $C_1$–$C_2$ haloalkyl, $C_1$–$C_2$ alkoxy, $C_1$–$C_2$ alkylthio, or $C_1$–$C_2$ alkylsulfonyl;

$R^1$ is hydrogen or $C_1$–$C_2$ alkyl;
$R^2$ is hydrogen or $C_1$–$C_2$ alkyl;
$R^3$ is hydrogen or $C_1$–$C_2$ alkyl; and
$R^4$ and $R^5$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^b SO_n$— wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^c R^d$ wherein $R^c$ and $R^d$ independently are hydrogen or $C_1$–$C_4$ alkyl; (11) $R^3 C(O)$- wherein $R^3$ is $C_1$–$C_4$ alkyl or $C_1$–$C_4$ alkoxy; or (12) —$SO_2 NR^c R^d$ wherein $R^c$ and $R^d$ are as defined; and (13) —$N(R^c)C(O)R^d$ wherein $R^c$ and $R^d$ are as defined.

9. The method of claim 8 wherein R is chlorine, bromine, methyl, nitro or trifluoromethyl; $R^1$, $R^2$ and $R^3$ are hydrogen or methyl; and $R^5$ and $R^6$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^b SO_n$— wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^c R^d$ wherein $R^c$ and $R^d$ independently are hydrogen or $C_1$–$C_4$ alkyl; (11) $R^e C(O)$ wherein $R^e$ is $C_1$–$C_4$ alkyl or $C_1$–$C_4$ alkoxy; or (12) $SO_2 NR^c R^d$ wherein $R^c$ and $R^d$ are as defined; or (13) —N—$(R^c)$-$C(O)R^d$ wherein $R^c$ and $R^d$ are as defined.

10. The method of claim 9 wherein $R^4$ and $R^5$ independently are hydrogen; chlorine; fluorine bromine; methyl; $C_1$–$C_4$ alkoxy; trifluoromethoxy; cyano; nitro; trifluoromethyl; $R^b SO_n$— wherein n is the integer 0 or 2 and $R^b$ is methyl, chloromethyl, wherein n is the integer 0 or 2 and $R^b$ is methyl, chloromethyl, trifluoromethyl, ethyl or n-propyl, $R^e C(O)$— wherein $R^e$ is $C_1$–$C_4$ alkyl; or $SO_2 CR^c R^d$ wherein $R^c$ and $R^d$ are as defined, and $R^4$ is in the 3-position and $R^5$ is in the 4-position.

11. The method of claim 9 wherein $R^4$ is hydrogen and $R^5$ is hydrogen, chlorine, bromine, fluorine, cyano, trifluoromethyl or $R^b SO_2$ wherein $R^b$ is $C_1$–$C_4$ alkyl or $C_1$–$C_4$ haloalkyl.

12. The method of claim 9 wherein R is nitro, $R^1$ is hydrogen; $R^2$ is hydrogen; $R^3$ is hydrogen; $R^4$ is hydrogen; and $R^5$ is trifluoromethyl.

13. The method of claim 9 wherein R is nitro; $R^1$ is hydrogen; $R^2$ is hydrogen; $R^3$ is hydrogen; $R^4$ is hydrogen; and $R^5$ is methylsulfonyl.

14. The method of claim 9 wherein R is nitro; $R^1$ is hydrogen; $R^2$ is methyl; $R^3$ is methyl; $R^4$ is hydrogen; and $R^5$ is ethylsulfonyl.

15. A herbicidal composition comprising an herbicidally active compound of the formula

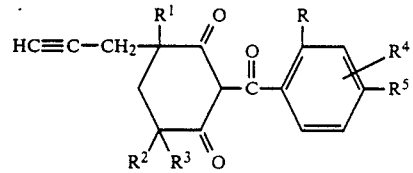

wherein

R is halogen, $C_1$–$C_2$ alkyl, nitro, $C_1$–$C_2$ haloalkyl, $C_1$–$C_2$ alkoxy, $C_1$–$C_2$ alkylthio, or $C_1$–$C_2$ alkylsulfonyl;

$R^1$ is hydrogen or $C_1$–$C_2$ alkyl;
$R^2$ is hydrogen or $C_1$–$C_2$ alkyl;
$R^3$ is hydrogen or $C_1$–$C_2$ alkyl; and
$R^4$ and $R^5$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^b SO_n$— wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^c R^d$ wherein $R^c$ and $R^d$ independently are hydrogen or $C_1$–$C_4$ alkyl; (11) $R^3 C(O)$- wherein $R^3$ is $C_1$–$C_4$ alkyl or $C_1$–$C_4$ alkoxy; or (12) —$SO_2 NR^c R^d$ wherein $R^c$ and $R^d$ are as defined; and (13) —$N(R^c)C(O)R^d$ wherein $R^c$ and $R^d$ are as defined; or its salt; and an inert carrier therefor.

16. The composition of claim 1 wherein R is chlorine, bromine, methyl, nitro or trifluoromethyl; $R^1$, $R^2$ and $R^3$ are hydrogen or methyl; and $R^5$ and $R^6$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^b SO_n$— wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^c R^d$ wherein $R^c$ and $R^d$ independently are hydrogen or $C_1$–$C_4$ alkyl; (11) $R^e C(O)$ wherein $R^e$ is $C_1$–$C_4$ alkyl or $C_1$–$C_4$ alkoxy; or (12) $SO_2 NR^c R^d$ wherein $R^c$ and $R^d$ are as defined; or (13) —N—$(R^c)$-$C(O)R^d$ wherein $R^c$ and $R^d$ are as defined.

17. The composition of claim 15 wherein $R^4$ and $R^5$ independently are hydrogen; chlorine; fluorine; bromine; methyl; $C_1$–$C_4$ alkoxy; trifluoromethoxy; cyano; nitro; trifluoromethyl; $R^b SO_n$—wherein n is the integer 0 or 2 and $R^b$ is methyl, chloromethyl, trifluoromethyl, ethyl or n-propyl, $R^e C(O)$— wherein $R^e$ is $C_1$–$C_4$ alkyl; or $SO_2 CR^c R^d$ wherein $R^c$ and $R^d$ are as defined, and $R^4$ is in the 3-position and $R^5$ is in the 4-position.

18. The composition of claim 15 wherein $R^4$ is hydrogen and $R^5$ is hydrogen, chlorine, bromine, fluorine, cyano, trifluoromethyl or $R^b SO_2$ wherein $R^b$ is $C_1$–$C_4$ alkyl or $C_1$–$C_4$ haloalkyl.

19. The composition of claim 15 wherein R is nitro, $R^1$ is hydrogen; $R^2$ is hydrogen; $R^3$ is hydrogen; $R^4$ is hydrogen; and $R^5$ is trifluoromethyl.

20. The composition of claim 15 wherein R is nitro; $R^1$ is hydrogen; $R^2$ is hydrogen; $R^3$ is hydrogen; $R^4$ is hydrogen; and $R^5$ is methylsulfonyl.

21. The composition of claim 15 wherein R is nitro; $R^1$ is hydrogen; $R^2$ is methyl; $R^3$ is methyl; $R^4$ is hydrogen; and $R^5$ is methylsulfonyl.

* * * * *

UNITED STATES PATENT AND TRADEMARK OFFICE
CERTIFICATE OF CORRECTION

PATENT NO. : 4,997,473
DATED : March 5, 1991
INVENTOR(S) : Nhan H. Nguyen

It is certified that error appears in the above-indentified patent and that said Letters Patent is hereby corrected as shown below:

In Column 16, line 9, delete "(8) $C-C_{nitro}$".

In Column 16, line 11, after the word "and" insert --$R^b$--.

In Column 17, line 61, "ethylsulfonyl" should read --methylsulfonyl--.

Signed and Sealed this

Tenth Day of May, 1994

Attest:

BRUCE LEHMAN

*Attesting Officer*  *Commissioner of Patents and Trademarks*